(12) United States Patent
Trapp (10) Patent No.: US 9,320,831 B2
(45) Date of Patent: Apr. 26, 2016

(54) POLYMER SHRINK TUBES AND NOVEL USES THEREFOR

(75) Inventor: Benjamin M. Trapp, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 553 days.

(21) Appl. No.: 11/073,053

(22) Filed: Mar. 4, 2005

(65) Prior Publication Data

US 2006/0198976 A1    Sep. 7, 2006

(51) Int. Cl.
*B29C 47/00* (2006.01)
*B32B 1/08* (2006.01)
*A61L 29/04* (2006.01)

(52) U.S. Cl.
CPC .......... *A61L 29/04* (2013.01); *A61L 29/041* (2013.01); *Y10T 428/139* (2015.01)

(58) Field of Classification Search
CPC .... A61L 29/04; A61L 29/041; Y10T 428/139
USPC ......... 428/36.9, 36.91; 138/121, 128; 156/85, 156/86; 604/523
See application file for complete search history.

(56) References Cited

U.S. PATENT DOCUMENTS

| | | |
|---|---|---|
| 3,498,286 A | 3/1970 | Koester et al. |
| 3,953,566 A | 4/1976 | Gore |
| 4,187,390 A | 2/1980 | Gore |
| 4,265,848 A | 5/1981 | Rusch |
| 4,648,871 A | 3/1987 | Jacob |
| 5,048,572 A * | 9/1991 | Levine .................. 138/121 |
| 5,275,208 A * | 1/1994 | Lawrence .................. 138/121 |
| 5,357,955 A * | 10/1994 | Wolf et al. .................. 600/341 |
| 5,423,773 A | 6/1995 | Jimenez |
| 5,476,589 A | 12/1995 | Bacino |
| 5,609,624 A | 3/1997 | Kalis |
| 5,693,015 A * | 12/1997 | Walker et al. .............. 604/96.01 |
| 5,755,704 A | 5/1998 | Lunn |
| 5,882,347 A | 3/1999 | Mouris-Laan et al. |
| 5,897,537 A | 4/1999 | Berg et al. |
| 5,951,929 A | 9/1999 | Wilson .................. 264/139 |
| 5,954,702 A * | 9/1999 | Lal et al. .................. 604/533 |
| 5,972,441 A * | 10/1999 | Campbell et al. .............. 428/34.1 |
| 6,016,848 A * | 1/2000 | Egres, Jr. .................. 138/137 |

(Continued)

FOREIGN PATENT DOCUMENTS

| | | |
|---|---|---|
| EP | 0 377 749 | 7/1990 |
| EP | 0692276 | 1/1996 |

(Continued)

OTHER PUBLICATIONS

Integral. (2012) retrived May 31, 2012, from http://dictionary.reference.com/browse/integral?s=t.*

(Continued)

*Primary Examiner* — Gwendolyn Blackwell
*Assistant Examiner* — Kevin Ortman, Jr.
(74) *Attorney, Agent, or Firm* — Faegre Baker Daniels LLP (57) ABSTRACT

Novel polymer shrink tubes, such as fluoropolymer shrink tubes and novel uses thereof. The polymer shrink tubes include at least one three-dimensional pattern formed along at least a portion of the inner surface of the tube. The polymer shrink tubes can be used for, for example, embossing a pattern into a polymer tube. Further use includes, for example, forming a catheter with at least one channel located in the catheter wall.

11 Claims, 4 Drawing Sheets

(56) References Cited

U.S. PATENT DOCUMENTS

| | | | |
|---|---|---|---|
| 6,019,753 A * | 2/2000 | Pagan | 604/523 |
| 6,059,769 A | 5/2000 | Lunn et al. | |
| 6,206,868 B1 | 3/2001 | Parodi | |
| 6,280,413 B1 | 8/2001 | Clark et al. | 604/104 |
| 6,280,545 B1 | 8/2001 | Kanesaka | 156/84 |
| 6,295,989 B1 | 10/2001 | Connors, III | |
| 6,423,032 B2 | 7/2002 | Parodi | |
| 6,540,712 B1 | 4/2003 | Parodi et al. | |
| 6,863,757 B1 | 3/2005 | Gonzalez et al. | |
| 2002/0049426 A1 | 4/2002 | Butler et al. | 604/892.1 |
| 2003/0040694 A1 | 2/2003 | Dorros et al. | |
| 2003/0040704 A1 | 2/2003 | Dorros et al. | |
| 2003/0040705 A1 | 2/2003 | Dorros et al. | |
| 2004/0193139 A1 | 9/2004 | Armstrong et al. | |

FOREIGN PATENT DOCUMENTS

| | | |
|---|---|---|
| EP | 1 004 327 | 5/2000 |
| JP | S53-139390 | 12/1978 |
| JP | 56-144126 | 11/1981 |
| JP | H06-004301 | 6/1990 |
| JP | H06-142207 | 5/1994 |
| JP | H08-024342 | 1/1996 |
| JP | H08-206218 | 8/1996 |
| JP | H09-501759 | 2/1997 |
| JP | H10-026266 | 1/1998 |
| JP | H10-118188 | 5/1998 |
| JP | 2000-225196 | 8/2000 |
| JP | 2001-079095 | 3/2001 |
| JP | 2001-112870 | 4/2001 |
| JP | 2002-517291 | 6/2002 |
| WO | 95/05555 | 2/1995 |
| WO | 95-05555 | 2/1995 |
| WO | 99/64097 | 12/1999 |
| WO | 01/13982 | 3/2001 |

OTHER PUBLICATIONS

Ebnesajjad, S. vol. 2: Melt processible fluoropolymers the definitive user's guide and databook. In: *Fluoroplastics*, Plastics Design Library: New York: 2003; 220-221.

* cited by examiner

POLYMER SHRINK TUBES AND NOVEL USES THEREFOR

FIELD OF THE INVENTION

This invention relates to polymer shrink tubing. Such shrink tubing can be used for, among other things, the manufacture of catheters.

DESCRIPTION OF RELATED ART

The use of delivery catheters to provide various treatments to a patient is well known. Such delivery catheters have a variety of well-known uses such as, for example, PTA and PTCA treatment, stent delivery, etc. Many delivery catheters are guided to the treatment location through a previously placed guide catheter. Moreover, it is also known to advance diagnostic catheters, angiographic catheters, and steerable catheters to a treatment location through a previously placed guide catheter.

The guide catheter will typically have a centrally located lumen, with the delivery catheter passed through the centrally located lumen to the treatment site. In view of this, it is common for the inner surface of the guide catheter that defines the centrally located lumen to be comprised of a low friction material, such as polytetrafluoroethylene (PTFE). Moreover, to provide structural support guide catheters usually are metal reinforced using, for example, a metal braid or coil wrapped about the low friction material. It is not uncommon for the metal reinforcement to be embedded by an outer polymer material that defines the outer wall portion of the guide catheter.

Recently, it has been suggested to use guide type catheters for certain stroke therapies, wherein the guide catheter is delivered, for example, to a patient's carotid artery. Various treatment devices, such as delivery catheters, balloon-on-a-wire devices, thrombectomy removal devices, etc., can be guided to the treatment site through one or more lumens provided in the guide catheter. Moreover, such guide catheters can include an inflatable member at the distal end thereof to occlude blood flow in the selected carotid artery.

Examples of such stroke therapy catheter constructions are illustrated in, for example, commonly owned U.S. Pat. Nos. 6,206,868; 6,423,032; 6,540,712; and 6,295,989.

Such catheter constructions can present manufacturing challenges. For example, catheter constructions as shown, for example, in commonly owned U.S. Patent Application Publication Nos. 2003/0040704A1; 2003/0040694A1; and 2003/0040705A1, can include, for example, at least an inflation lumen in the catheter wall, which inflation lumen will be in communication with the inflatable member at the distal end of the catheter. Further, the catheter wall can be a polymer material that embeds a metal reinforcement. Moreover, a PTFE inner liner material can define a centrally located lumen.

Providing one or more lumens in the catheter wall of such constructions is extremely difficult. One method of providing lumens in the catheter wall is described in commonly owned and copending U.S. Patent Application Publication No. 2004/0193139, published Sep. 3, 2004, which discloses a polymer film wrapping process to produce such catheters. The catheter can be formed by placing a thin-walled PTFE liner tube over a mandrel. A wire support structure (e.g., braid, ribbon, coil, etc.) can then be placed over the thin-walled tube. Over the wire support structure is placed a thermoplastic material that is caused to embed the wire support structure. As taught in this commonly owned patent application, at least one lumen, or channel, in the catheter wall can be formed by a laser cut into a thermoplastic material defining the outer catheter wall. Thereafter, a polymer film is applied to (e.g., wrapped about) the catheter wall to close the channel and form the longitudinally extending lumen in the catheter body. Another method of forming lumens in the catheter wall includes, for example, placing a small, hollow tube, such as polyimide tube, adjacent the wire support structure and then embedding the wire support structure and small tube into the thermoplastic material.

The present invention provides, among other things, unique methods of forming such catheter constructions that overcome the problems discussed above.

SUMMARY OF THE INVENTION

The invention relates to polymer shrink tubing and novel uses therefore. One aspect of the invention is a tube comprising a fluoropolymer shrink tube having an inner surface and at least one three-dimensional pattern formed along at least a portion of the inner surface of the tube. In an aspect of the invention, the three-dimensional pattern comprises at least one rib formed along the inner surface. The at least one rib can be longitudinally extending, spirally extending, etc.

In a further aspect of the invention, the invention includes a tube comprising a polymer shrink tube having an inner surface and at least one rib formed along the inner surface, the rib extending from the inner surface and having a height of about 0.5 mils or less, more preferably less than about 0.2 mm.

A further aspect of the invention includes a catheter comprising an inner liner comprising fluoropolymer (e.g., PTFE) tubing. Preferably the fluoropolymer tube is an extruded PTFE tube. The tube having a proximal end, a distal end, an inner surface and an outer surface; an outer polymer tube having a proximal end, a distal end, an inner surface and an outer surface, wherein the inner surface of the outer polymer tube is positioned over the outer surface of the fluoropolymer tube; wherein at least one channel is formed in the outer polymer tube, the at least one channel preferably measuring about 7 by about 15 mils (0.007"×0.015") and extending for at least a portion and preferably a majority of the length of the catheter; and polymer film covering at least a portion and preferably a majority of the length of the at least one channel, thus forming a lumen in the outer polymer tube.

In a still further aspect of the invention, the invention includes a method of creating an external, embossed pattern on the exterior of a cylindrical device comprising: providing a polymer tube having at least one exterior surface; providing a polymer shrink tube having an inner and an outer surface, the inner surface having at least one three-dimensional pattern thereon; placing the polymer shrink tube around the polymer tube; applying sufficient energy to the shrink tube so as to shrink the shrink tube around the exterior of the polymer tube while causing at least a portion of the at least one three-dimensional pattern to become embossed into the exterior surface of the polymer tube. The applied energy softens the polymer tube material and shrinks the shrink tube, thus leading to embossing the pattern into the polymer tube. This method is particularly suitable for forming catheters such as the guide catheters discussed above.

DESCRIPTION OF THE DRAWINGS

The operation of the present invention should become apparent from the following description when considered in conjunction with the accompanying drawings in which.

DETAILED DESCRIPTION OF THE INVENTION

Figure 1:
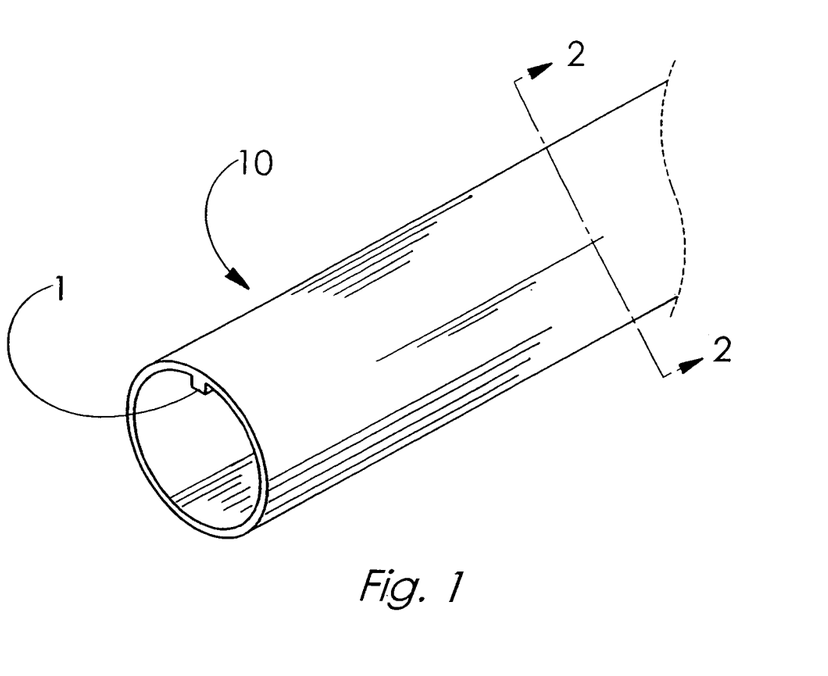
FIG. 1 shows in partial perspective view a polymer shrink tube according to the present invention.
Figure 2:
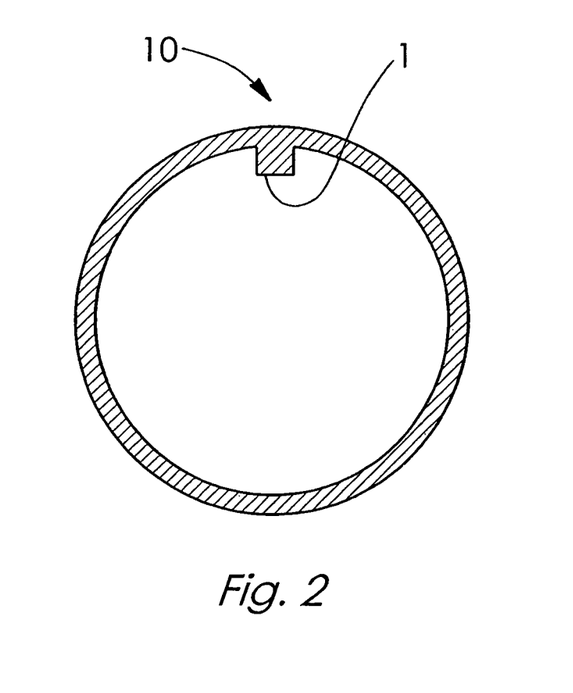
FIG. 2 is a schematic cross-section taken along lines 2-2 of FIG. 1.

A first aspect of the invention is a tube comprising a fluoropolymer shrink tube having an inner surface and at least one three-dimensional pattern formed along at least a portion of the inner surface of the tube. In a further aspect of the invention, the three-dimensional pattern can comprise at least one rib (such as at least one longitudinally extending rib) formed along the inner surface of the tube. Suitable fluoropolymer materials include, for example, fluorinated ethylene propylene (FEP), fluoroelastomers such as VITON® fluoroelastomers (DuPont Dow Elastomers), ethylene tetrafluoroethylene (ETFE), perfluoroalkoxy (PFA), and polytetrafluoroethylene (PTFE). The fluoropolymer shrink tube is shown in partial perspective view in FIG. 1. FIG. 2 is a cross-section schematic drawing taken along lines 2-2 of FIG. 1. As shown in the figures, the three-dimensional pattern formed along at least a portion of the inner surface of the tube 10 is indicated by 1, and in this case, is a longitudinally extending rib which can extend for essentially the entire length of the tube. Other three-dimensional patterns are envisioned by the present invention, such as, for example, spirally extending ribs, as well as a plurality of three-dimensional patterns, such as two or more ribs.

By "shrink tube having at least one three-dimensional pattern formed along at least a portion of the inner surface of the tube" it is meant to include longitudinally extending, hollow tubes having at least one protuberance, recess, or otherwise three-dimensional pattern, on the inner surface of the tube. The tube will exhibit some shrinkage of its inner diameter upon exposure to suitable energies, such as heat. Longitudinal shrinkage is not a requirement according to the invention, although it may be desirable. Therefore, "shrink tube" will include a polymer tube that will exhibit some shrinkage of its inner diameter upon exposure to suitable energy and may also exhibit some longitudinal shrinkage upon exposure to suitable energy. It is desirable for the shrink tube to shrink in a predictable manner such that the three-dimensional pattern is predictably retained upon exposure to the suitable energy.

Polymer shrink tubes can be made by, for example, well-known extrusion processes. Typically such tubes will be formed having a first inner diameter. The tube is then expanded to a second inner diameter (referred to as the "expanded inner diameter"). Upon application of suitable energy the inner diameter will shrink back to about the first inner diameter (referred to as the "retracted inner diameter").

As stated above, the shrink tubes can comprise, for example, the fluoropolymer materials listed above. The fluoropolymer shrink tubes will shrink when heated to an appropriate temperature or exposed to other suitable energy forms. For example, the following shrink tubes will shrink at about the listed temperature or temperature range. VITON® fluoroelastomer, about 120° C.; ETFE, about 175° C.; PFA, about 204° C.; FEP, from about 210 to about 260° C.; PTFE, from about 325 to about 340° C. A particularly attractive fluoropolymer tube comprises FEP.

In a further aspect of the invention, the invention includes a catheter comprising an inner liner comprising fluoropolymer (e.g., PTFE) tubing having a proximal end, a distal end, an inner surface defining a generally centrally located catheter lumen and an outer surface; an outer polymer tube having a proximal end, a distal end, an inner surface, and an outer surface; wherein the inner surface of the outer polymer tube is positioned over the outer surface of the fluoropolymer tube; wherein further at least one longitudinally extending channel is formed in the outer polymer tube, the at least one channel (preferably measuring about 7 by about 15 mils) extending for at least a portion and preferably a majority of the length of the catheter; and polymer film covering at least a portion and preferably a majority of the length of the at least one channel; thus defining a longitudinally extending lumen in the catheter wall. Preferably, the catheter is a delivery catheter having an about 9 French or less outer diameter, even more preferably an about 8 French or less outer diameter. In an aspect of the invention the catheter wall has a thickness of about 15 mil or less, and preferably about 10 mil or less, for at least a portion of its length, and preferably over substantially its entire length. The at least one channel can be formed using polymer shrink tube. In an aspect of the invention the polymer shrink tube has an expanded inner diameter of about 0.150 inch over substantially the entire length of the tube. In a further aspect of the invention the polymer shrink tube has a retracted inner diameter of about 0.100 inch over substantially the entire length of the tube. In a still further aspect of the invention, the at least one channel can be formed using fluoropolymer shrink tube, as discussed above. The fluoropolymer tube can comprise any suitable fluoropolymer as discussed above and may have an expanded inner diameter of about 0.150 inch over substantially the entire length of the tube and may also have a retracted inner diameter of about 0.100 inch over substantially the entire length of the tube. Other polymer shrink tube may be used, such as olefins, including chlorinated olefins, polyethylene terephthalate (PET), and polyvinyl chloride (PVC).

The outer polymer tube can comprise any suitable polymer. Preferred polymers include thermoplastics such as PEBAX® polyether block amides, nylon, urethanes, polyethylene, polypropylene, FEP, etc. Particularly preferred for the outer polymer tube is a material comprising PEBAX® polyether block amides, such as PEBAX® 6333.

It should be understood that although the inner surface of the outer polymer tube is positioned over the outer surface of the fluoropolymer tube, there is no requirement that the tube surfaces directly contact each other. It may be desirable to provide an adhesive between these materials. Moreover, a reinforcing material such as a metal (e.g., stainless steel or nitinol) or polymer support structure such as braiding, coil, stylets, tubing, ribbon, or what-have-you can be positioned between the tube surfaces to obtain desired properties. It may be desirable for the outer polymer tube to at least partially embed any reinforcing material (e.g. metal braid). Moreover, it may be desirable for the outer polymer to flow through the reinforcement and bond to the fluoropolymer tube. In such a case, the fluoropolymer tube outer surface can be chemically etched to aid in the adhesion between the outer polymer tube and fluoropolymer tube.

The polymer film which can cover the at least one channel, can comprise any suitable polymer film material.

For example, the film material can be made from a thin tape of porous expanded polytetrafluoroethylene (ePTFE) that can be helically wrapped about the exterior of the catheter shaft. Preferred ePTFE films are generally made as taught by U.S. Pat. Nos. 3,953,566 and 4,187,390 to Gore. Even more preferred ePTFE films can be made as taught by U.S. Pat. No. 5,476,589 to Bacino. Further examples of polymer films include polyethylene (including ultra-high molecular weight polyethylene), polypropylene, polyamide, polyethylene terephthalate, fluorinated ethylene propylene (FEP), perfluoroalkoxy resin, polyurethane, polyester, polyimide, etc.

Most preferably, the wrapping is accomplished in two opposing directions parallel to the length of the outer polymer tube, resulting in a bias-ply construction. Although helically wrapping a tape of polymer film is a preferred embodiment, it is also possible to provide the polymer film as a thin tubular structure that can coaxially enclose the entire outer polymer tube. Moreover, it is also possible to provide a strip of thin polymer tape material that covers the channel and is adhered to the surface of the outer polymer tube immediately adjacent both sides of the channel. Suitable wrapping techniques are fully described in, for example, commonly owned and co-pending U.S. Patent Application Publication No. 2004/193139, published Sep. 30, 2004. As described in the commonly owned application, the porous polymer tape can optionally be provided with a thin, non-porous coating. Moreover, prior to wrapping the polymer tube, it may be desirable to fill the channel (at least partially or completely) with a material that will provide structural support to the at least one channel so that the dimensions of the channel will not be substantially altered by the film wrapping process. Of course, materials that can be easily removed from the channel after film wrapping is completed are preferred and will be apparent to the skilled artisan.

The polymer tape is most preferably made from a thin porous expanded PTFE film that has been provided with a porous or non-porous coating of, or is at least partially imbibed with, a thermoplastic such as a thermoplastic fluoropolymer, and preferably EFEP (ethylene tetra fluoro ethylene based copolymer, available from Daikin America). An example of a suitable wrapping technique includes using EFEP in combination with ePTFE tape. The tape can have, for example, a width of about 6 mm and a thickness of about 0.005 mm. The ePTFE film can be provided with a non-porous coating of EFEP on one or both sides. Moreover, the porosity of the ePTFE film can be at least partially or substantially completely imbibed with EFEP. After the coated and/or imbibed film is cut into narrow tape, the tape can be helically wrapped about the outer polymer tube comprising PEBAX® polyether block amide. The wrapped catheter can then be heated for about 5 minutes in a convection oven set at about 160° C. to melt-bond the helically wrapped layers of the film together. Thereafter, the catheter can be removed from the oven and cooled to room temperature.

In an alternative embodiment, rather than using EFEP, a UV-curable or other light or radiation curable polymer could be used, thus allowing for curing of the polymer without application of such high temperature.

In a preferred embodiment, the polymer comprises UV-curable polymer. UV-curable is defined as a material that will react under UV light to either cure or form a durable bond. The UV light can be provided by a lamp having a suitable voltage, a suitable strength, and a suitable wavelength. Curing with UV light may be carried out for any suitable length of time, and the distance between the sample being cured and the UV lamp can be any suitable distance. All of the above parameters will be readily determinable by one skilled in the art. In an aspect of the invention the UV curable material can also be sensitive to visible light. However, preferred conditions are present only under the UV spectrum (100-400 nm). The preferred range is in the UVA spectrum (320-390 nm). Suitable UV-curable polymers include, for example, acrylated epoxies, acrylates, urethane acrylates, urethane methacrylates, silanes, silicones, epoxides, epoxy methacrylates, triethylene glycol diacetate, and vinyl ethers. Specific examples of these polymers include acrylated aliphatic oligomers, acrylated aromatic oligomers, acrylated epoxy monomers, acrylated epoxy oligomers, aliphatic epoxy acrylates, aliphatic urethane acrylates, aliphatic urethane methacrylates, alkyl methacrylate, amine-modified oligoether acrylates, amine-modified polyether acrylates, aromatic acid acrylate, aromatic epoxy acrylates, aromatic urethane methacrylates, butylene glycol acrylate, stearyl acrylate, cycloaliphatic epoxides, cylcohexyl methacrylate, ethylene glycol dimethacrylate, epoxy methacrylates, epoxy soy bean acrylates, glycidyl methacrylate, hexanediol dimethacrylate, isodecyl acrylate, isooctyl acrylate, oligoether acrylates, polybutadiene diacrylate, polyester acrylate monomers, polyester acrylate oligomers, polyethylene glycol dimethacrylate, stearyl methacrylate, triethylene glycol diacetate, and vinyl ethers. Preferred UV-curable polymers include, for example, medical grade UV-curable polymers such as DYMAX® 204 CTH UV-curable polymer and DYMAX® 206 CTH UV-curable polymer (both commercially available medical grade UV-curable polymers available from DYMAX Corporation, Torrington, CT).

In addition to EFEP and UV-curable polymers, further suitable polymer materials can include, for example, thermoplastics, thermosets, pressure sensitive adhesives, heat-activated adhesives, and chemically activated adhesives.

Preferred polymer materials include thermoplastics that melt below the temperature that would cause the outer tube and/or polymer film to melt. This allows the polymer tape wraps (when used) to fuse together without melting the polymer tape, without reflowing the outer polymer tube and, thus, without losing the pattern embossed into the outer polymer tube. UV-curable adhesives can be particularly attractive in this aspect of the invention. Particularly attractive are medical grade UV-curable polymers, such as the above-mentioned DYMAX® 204 CTH and DYMAX® 206 CTH.

The particular polymer used will, of course, depend upon the particular embodiment and desired results. Such polymers can be provided in liquid or solid form. In an aspect of the invention, polymers include, for example, THV (tetrafluoroethylene, hexafluoropropylene, and vinylide fluoride, available from Dyneon), EFEP (Daikin America), PE (polyolefin), polyamides, polyacryl-amides, polyesters, polyolefins (e.g., polyethylene), polyurethanes, and the like.

Suitable polymer application means include any method known in the art. With regard to porous polymer films, suitable application means include, for example, coating techniques (e.g., dip coating), solvent imbibing, vacuum assisted coating, pressure assisted coating, nip coating, and other suitable means which result in the polymer filling at least some of the porosity of the porous polymer film.

It may be desirable to utilize a solvent to aid in providing polymer to the porosity of the polymer film. The ratio of solvent material to polymer can vary and will be readily determinable by the skilled artisan. A 50/50 by weight solvent to polymer solution may be particularly acceptable. Preferable solvent materials will be readily apparent to one skilled in the art and include, for example, alcohols, ketones, etc. Methyl ethyl ketone (MEK) may be one particularly attractive solvent. When a solvent material is utilized, the solvent material can be easily removed or driven off once the polymer is provided to at least some of the porosity of the porous film as desired.

The invention also relates to a method for forming catheters having at least one lumen located in the catheter wall and extending for at least a portion of the length of the catheter. The at least one lumen can be formed by utilizing the polymer shrink tubing, and particularly fluoropolymer shrink tubing, according to the present invention. The invention further relates to a method of forming catheters having easily tailorable properties and/or altered cross-sections.

For example, a cylindrical, flowable plastic material (such as Pebax® polyether block amides), having a generally central, longitudinally extending lumen, is provided. In an aspect of the invention, a cylindrical mandrel having a diameter equal to about the desired inner diameter of a tubular member such as a catheter can first be provided. The outer surface of the mandrel can be coated with a lubricious material, such a PTFE. The cylindrical, flowable plastic material optionally could first be located over the mandrel to provide structural support to the flowable plastic material during further processing. Furthermore, a suitable, cylindrical polymer shrink tube having an inner and an outer surface, with the inner surface having at least one three-dimensional pattern thereon, can be placed over the flowable plastic tube. Thereafter, a suitable energy source, such as hot air can be applied to the shrink tube to shrink the tube around the outer surface of the flowable plastic tube, causing the at least one three-dimensional pattern to be embossed into the flowable plastic tube. The temperature (and duration of application of heat) should be sufficient to shrink the tubing and cause the pattern to be embossed into the flowable plastic tube, but not so high (and/or so long in duration) as to cause the three-dimensional pattern to lose its form.

Figure 3:
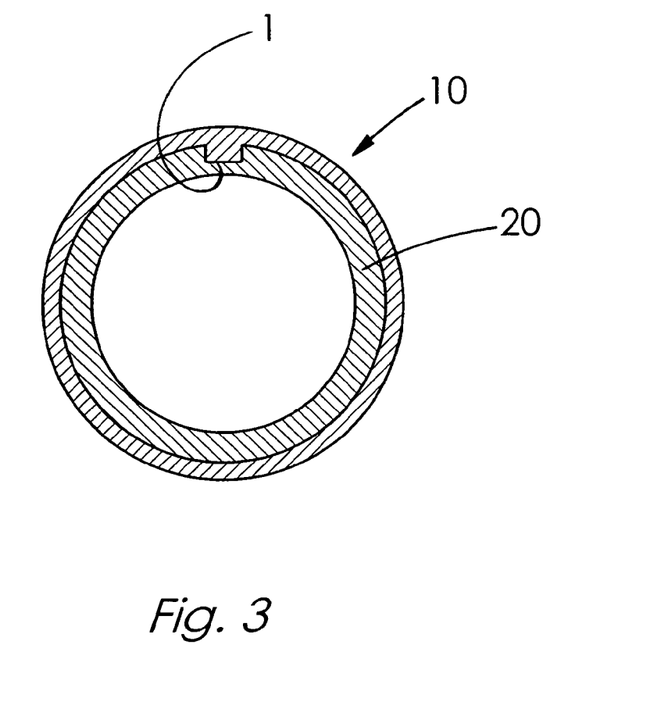
FIG. 3 is a schematic cross-section of the use of a polymer shrink tube according to the invention.

This embodiment is demonstrated in FIG. 3, where three-dimensional pattern 1 is a longitudinally extending rib on the inner surface of shrink tube 10. As can be seen, longitudinally extending rib 1 extends into flowable plastic tube 20 during and after the heating step described above. When shrink tube 10 is removed, a catheter body having a tailored cross-section is obtained, in this case a non-circular cross-section due to the longitudinally extending channel formed in the plastic tube. This will, of course, alter certain properties of the catheter body, such as bending characteristics, when compared to catheters without the longitudinally extending channel. It should be understood that other three-dimensional patterns could be embossed into the flowable plastic tube to result in various tailored cross-sections and result in various altered catheter properties.

Figure 4:
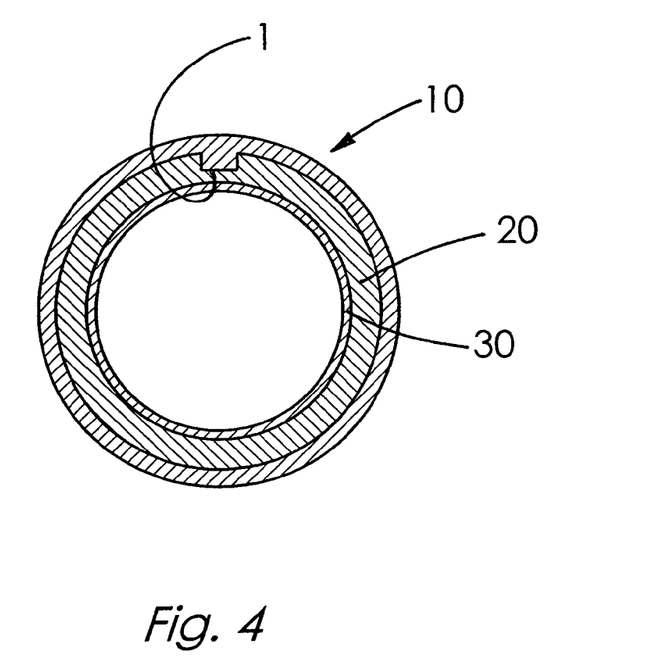
FIG. 4 is a schematic cross-section of a further use of a polymer shrink tube according to the present invention.
Figure 5:
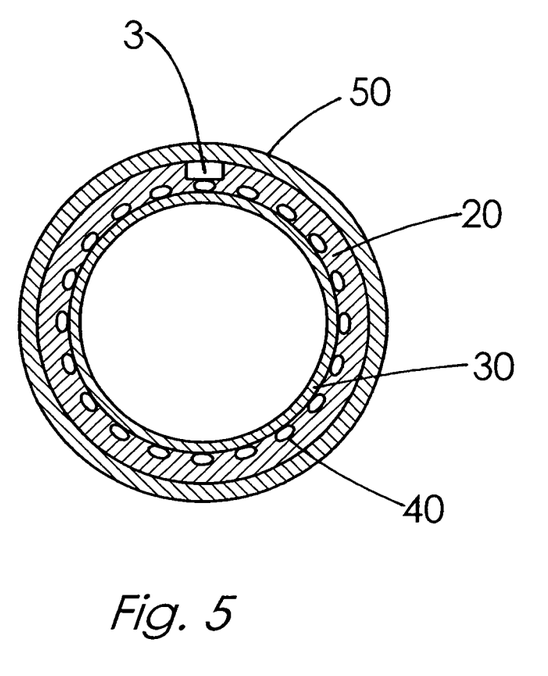
FIG. 5 is a schematic cross-section of a catheter according to the present invention.

FIG. 4 shows an alternative embodiment, which further comprises a thin-walled (e.g., about 1.5 mil wall thickness) tubular liner 30 of a suitable material (such as PTFE) as the inner member of the tubular structure. Obviously, this embodiment can be obtained by first placing the thin-walled liner over the mandrel (if used) and then following the sequence described above. FIG. 5 shows, in cross section, a further alternative embodiment which further includes metal coil (such as stainless steel or nitinol coil) material 40 located between the inner, thin-walled liner 30 and the flowable plastic tube 20. Of course, the metal coil could be at least partially embedded into the flowable plastic tube, as discussed above. In an aspect of the invention the metal coil is a helically wrapped stainless steel coil measuring about 0.002"×0.012" that can extend any desired length of the tube. As mentioned above, the metal coil material 40 could be substituted with any desirable reinforcing material, which will be readily apparent to those skilled in the art.

In an aspect of the invention polymer shrink tube is used to cause the at least one three-dimensional pattern to be embossed into the flowable plastic tube and to cause or assist the flowable plastic to embed the optional reinforcing material. This is preferably accomplished during a single heating (or other energy application) step. For example, an extruded PTFE tube could be placed over a mandrel, as discussed above. A suitable reinforcing material, such as stainless steel or nitinol coil could be placed over the PTFE tube. A flowable plastic tube could be placed over the reinforcing material and then a polymer shrink tube having at least one three-dimensional pattern on the inner surface thereof could be placed over the flowable plastic tube. Suitable energy, such as heat, could then be applied to the assembly to cause the polymer shrink tube to shrink. As the tube shrinks, the flowable plastic tube can at least partially embed, or substantially completely embed, the metal reinforcement while, at the same time, the at least one three-dimensional pattern is embossed into the flowable plastic tube. The at least one three-dimensional pattern could be a longitudinally extending rib, which results in a longitudinally extending channel being embossed into the flowable plastic tube. After allowing the assembly to cool, the polymer shrink tube can be removed and the at least one pattern could be covered with polymer film, as discussed above.

As shown in FIG. 5, shrink tube 10 has been removed, thus resulting in longitudinally extending channel 3. Moreover, the outer polymer tube 20 has been provided with polymer film cover 50, thus defining a longitudinally extending lumen in the outer polymer tube 20. In an aspect of the invention, polymer film 50 is provided as a helical wrap of ePTFE at least partially imbibed with suitable polymer, such as UV curable polymer or EFEP, as described above.

It should be understood that any number of longitudinally extending channels could be provided to the embodiment discussed above, by providing a plurality of longitudinally extending ribs to the shrink tubing 10. In an aspect of the invention, four longitudinally extending channels, each about 90° apart, are provided. In a further aspect of the invention, each of the four channels has dimensions essentially equal to one another. In a further aspect of the invention, each channel has a width of about 0.015 inch and a depth of about 0.007 inch. Once covered with suitable polymer film, four longitudinally extending lumens would be obtained. These lumens could be used, for example, to deliver inflation fluid to an expandable member on a distal end of a catheter, to pass strings/wires/or fluids down the length of a catheter, to deliver electrical, sensing, mechanical steering, or device deployment devices, etc. Moreover, the lumen(s) could be used to locate at least one material in the catheter wall that will alter at least one property of the catheter. For example, a stiffening wire could be located in a lumen for part of the length of the catheter, or for the entire length of the catheter. The stiffening wire could be located in the lumen before or after providing the polymer film cover. Further, the lumen could be filled, partially or completely, with any suitable material (e.g., polymer, metal, etc.) to alter the catheter's stiffness along at least a portion of the length of the catheter. According to this aspect of the invention it is possible to produce catheters having varying properties (e.g., stiffness) along the length of the catheter.

Figure 6:
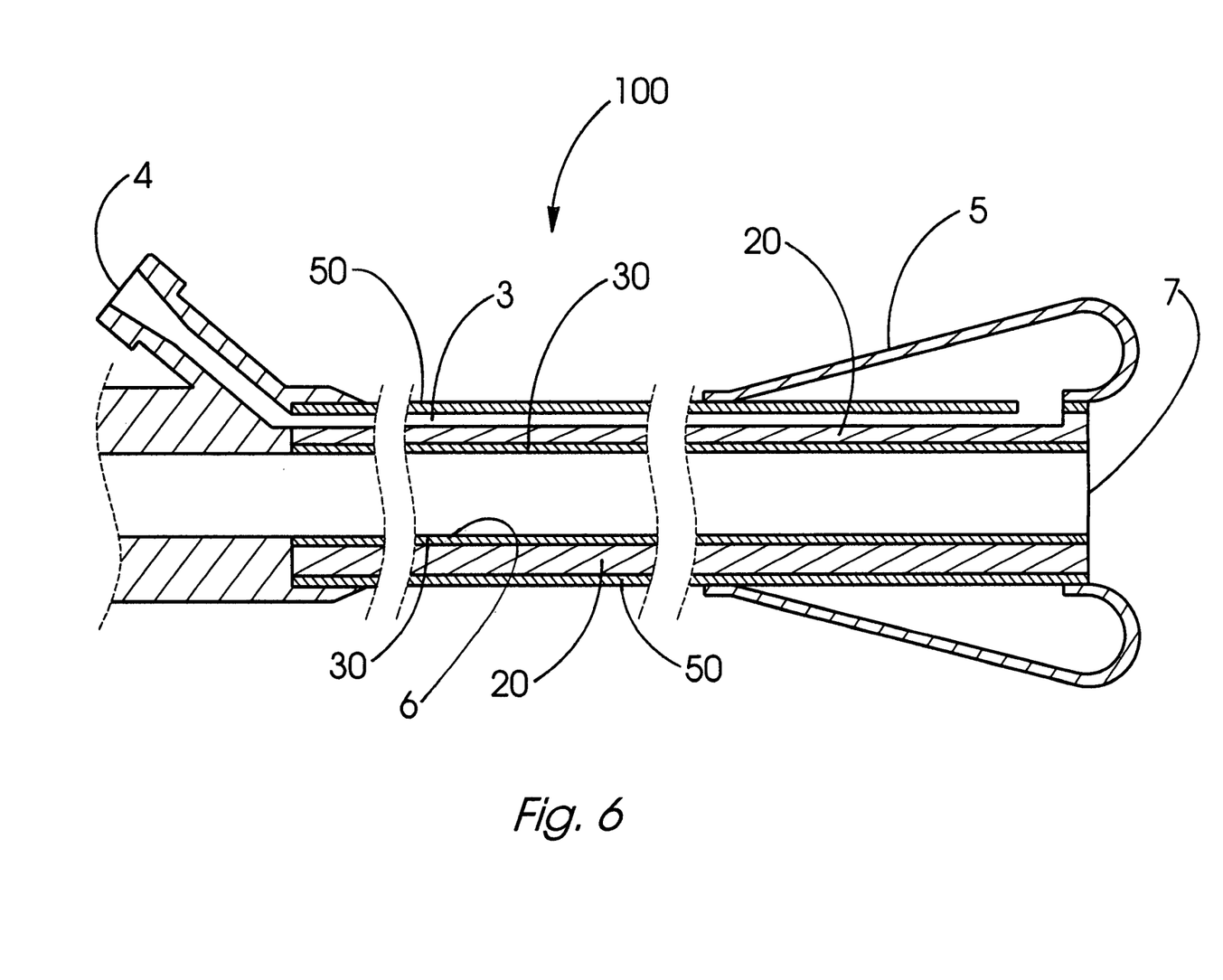
FIG. 6 is a longitudinal cross-section of a catheter according to the present invention.

Turning to FIG. 6, there is shown in longitudinal cross section, one potential catheter embodiment according to the present invention. As shown, the catheter 100 includes an inflatable member 5 located at the distal end 7 of the catheter. Thin-walled liner 30 (e.g., fluoropolymer such as PTFE) extends for the length of the catheter and defines inner, centrally located lumen 6. Positioned over the inner liner 30 is polymer tube 20, which also can extend for the length of the catheter. Not shown is optional reinforcing material, such as metal coil or braid (described above), which can also extend for the length of the catheter and be positioned over thin-walled liner 30 and optionally embedded into polymer tube 20. Polymer film wrap 50 can also extend for the length of the catheter and cover longitudinally extending channel 3, thus defining longitudinally extending lumen in polymer tube 20. As shown, longitudinally extending channel 3 can function as an inflation lumen and is in fluid communication with inflation port 4 and the interior of inflatable member 5.

As should be understood, catheter 100 can be appropriately sized for any number of desirable applications, such as those discussed in the commonly owned patents and patent applications, discussed above. Moreover, there is no requirement that an inflatable member is located at the distal end of the catheter, or provided at all. Furthermore, additional lumens could be provided in polymer tube 20. Such lumens could be used to allow for delivery of delivery catheters, balloon-on-a-wire devices, thrombectomy removal devices, steering wires, diagnostic catheters, angiographic catheters, etc., as well as to be used to locate at least one material in the catheter wall such as a stiffening wire, as discussed above.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A fluoropolymer shrink tube tubular construct comprising:
 a fluoropolymer shrink tube having a length, an inner surface, an outer surface, and a first wall thickness, at least one longitudinal rib formed along and extending essentially the entire length of the inner surface of the tube, wherein the at least one rib defines a second wall thickness that is greater than the first wall thickness; and
 a thermoplastic polymer tube surrounded by the fluoropolymer shrink tube, wherein due to the prior application of sufficient energy to the tubular construct, the fluoropolymer shrink tube was shrunken about an exterior surface of the thermoplastic polymer tube and embossed the at least one longitudinal rib onto the exterior surface of the thermoplastic polymer tube such that a channel is provided in the exterior surface of the thermoplastic tube that corresponds dimensionally to the shape of the longitudinal rib, the fluoropolymer shrink tube adapted to be removed from the thermoplastic polymer tube after being shrunken about the exterior surface to expose the channel in the thermoplastic polymer tube.

2. The fluoropolymer shrink tube of claim 1, wherein the at least one rib consists of one to four ribs.

3. The fluoropolymer shrink tube of claim 1, wherein the fluoropolymer comprises a material selected from the group consisting of fluorinated ethylene propylene, fluoroelastomers, ethylene tetrafluoroethylene, perfluoroalkoxy, and polytetrafluoroethylene.

4. The fluoropolymer shrink tube of claim 3, wherein the fluoropolymer comprises fluorinated ethylene propylene.

5. The fluoropolymer shrink tube of claim 1, wherein the fluoropolymer shrink tube has an expanded inner diameter of about 0.150" and a retracted inner diameter of about 0.100" over substantially the entire length of the fluoropolymer shrink tube.

6. The fluoropolymer shrink tube of claim 1 wherein the at least one rib has a height of less than about 0.5 mm.

7. The fluoropolymer shrink tube of claim 6, wherein the at least one rib has a height of less than about 0.2 mm.

8. A fluoropolymer shrink tube construct comprising a fluoropolymer shrink tube component having a length, an outer surface and an inner surface and at least one three-dimensional pattern formed along a least a portion of the inner surface of the shrink tube, said fluoropolymer shrink tube concentrically surrounding at least a portion of a length of a thermoplastic polymer tube such that the prior application of sufficient energy to the shrink tube caused the shrink tube to shrink and to emboss the at least one three-dimensional pattern onto an exterior surface of the thermoplastic polymer tube concentrically surrounded by the fluoropolymer shrink tube, the fluoropolymer shrink tube remaining unbonded to the thermoplastic polymer tube after being shrunken about the exterior surface of the thermopolastic polymer tube such that the fluoropolymer shrink tube is removable from around the thermoplastic polymer tube to expose the three-dimensional pattern on the outer surface of the thermoplastic polymer tube.

9. The fluoropolymer shrink tube of claim 8 wherein the fluoropolymer comprises a material selected from the group consisting of fluorinated ethylene propylene I fluoroelastomers, ethylene tetrafluoroethylene perfluoroalkoxyl and polytetrafluoroethylene.

10. The fluoropolymer shrink tube of claim 9 wherein the fluoropolymer comprises fluorinated ethylene propylene.

11. The fluoropolymer shrink tube of claim 8 wherein the three-dimensional pattern comprises at least one longitudinally extending rib.

* * * * *